United States Patent [19]

Matthews

[11] 4,410,271
[45] Oct. 18, 1983

[54] MULTIPLE-REFLECTION OPTICAL GAS CELL

[75] Inventor: Thomas G. Matthews, Oak Ridge, Tenn.

[73] Assignee: The United States of America as represented by the U.S. Department of Energy, Washington, D.C.

[21] Appl. No.: 274,014

[22] Filed: Jun. 15, 1981

[51] Int. Cl.³ .............................................. G01J 3/44
[52] U.S. Cl. .................................. 356/301; 356/318
[58] Field of Search ....................... 356/246, 301, 318

[56] References Cited

PUBLICATIONS

Benetti et al. "A New Optical System for Flame Spec. with Special Ref. to Thermally Assisted Anti-Stokes Fluorescence Applications", *Applied Spectroscopy*, vol. 25, #1, 1971, pp. 57–60.
Weber et al., J. Opt. Soc. Am., vol. 57 p. 19, 1967.
Anderson, "The Raman Effect", Marcel Decker Inc., New York, vol. 2, p. 581, 1973.
Witkowicz et al., Applied Optics vol. 14:3092 (1975).
Welsh et al., J. Opt. Soc. Am. vol. 41, p. 712, 1951.
Welsh et al., J. Opt. Soc. Am., vol. 45 p. 338, 1955.
Hill et al., Applied Optics, vol. 13 p. 186, 1974.
Hill et al., Applied Optics, vol. 16, p. 2004, 1977.
Muller, Optik, 56:1, 1980.
Konetak et al., Acta Physica Academiae Scientiarum Hungaricae Tomus, 48(4), pp. 409–414, 1980.

*Primary Examiner*—F. L. Evans
*Assistant Examiner*—L. Dietert
*Attorney, Agent, or Firm*—Edwin D. Grant; Stephen D. Hamel; Richard G. Besha

[57] ABSTRACT

A multiple-reflection optical cell for Raman or fluorescence gas analysis consists of two spherical mirrors positioned transverse to a multiple-pass laser cell in a confronting plane-parallel alignment. The two mirrors are of equal diameter but possess different radii of curvature. The spacing between the mirrors is uniform and less than half of the radius of curvature of either mirror. The mirror of greater curvature possesses a small circular portal in its center which is the effective point source for conventional F1 double lens collection optics of a monochromator-detection system. Gas to be analyzed is flowed into the cell and irradiated by a multiply-reflected composite laser beam centered between the mirrors of the cell. Raman or fluorescence radiation originating from a large volume within the cell is (1) collected via multiple reflections with the cell mirrors, (2) partially collimated and (3) directed through the cell portal in a geometric array compatible with F1 collection optics.

5 Claims, 4 Drawing Figures

MULTIPLE-REFLECTION OPTICAL GAS CELL

BACKGROUND OF THE INVENTION

This invention resulted from a contract with the United States Department of Energy.

It relates generally to the identification of chemical components in a gas mixture by detecting Raman or fluorescence radiation. More specifically, the invention relates to a new "multiple-reflection" optical cell design for (1) collecting Raman or fluorescence radiation from a large optical volume of gas sample excited by laser light and (2) focusing this radiation into a geometric array which is compatible with a conventional spectrometer.

In the pertinent literature, several multiple-reflection optical cells have been reported which enhance the sensitivity of Raman gas analysis through an improved optical collection efficiency for Raman-scattered radiation (see, for example, "The Raman Effect," Vol. 2, page 581, published by Marcel Decker, Inc., in 1973, and T. Witkowicz et al, *Applied Optics*, 14:3092, in 1975). Classical optical cells which predate the development of the laser were designed to collect radiation from gas samples excited by diffuse optical sources. A four-mirror (FIG. 1, A–D) multiple-reflection Raman cell positioned in a longitudinal mode along the axis of a large discharge lamp was described by Welsh et al in the *J. Opt. Soc. Am.*, 41:712 (1951) and 45:5 (1955). The mirrors of this cell (illustrated in FIG. 1) are semicircular and possess identical spherical radii of curvature. The mirrors are independently aligned and positioned in pairs spaced at a distance identical to the mirror radius of curvature. The spacing between each mirror-pair is large (greater than or equal to 2 meters) to accommodate long discharge lamps. The spacing between the two mirrors of each mirror-pair is a narrow slit. Only Raman radiation projecting in a near parallel alignment to the axis of the discharge lamp is collected and passed through the slit of a mirror-pair into collection optics for a spectrometer. Light emanating in all other directions is lost, limiting the optical collection efficiency of the cell.

With the advent of intense collimated optical excitation sources (lasers), the necessity of a "multiple-reflection" optical cell to enhance the sensitivity of laboratory-based Raman gas analyses has diminished. Several "multiple-pass" laser cells for Raman spectroscopy have been reported which are designed to optimize the intensity of a multiply reflected laser beam at one or two points in a gas sample. These multiple-pass cells have been positioned both inside and outside the cavity of a laser (see, for example, "The Raman Effect," Vol. 2, edited by A. Anderson and published by Marcel Decker, Inc., 1973, page 581). Multiple-pass cells exterior to the laser cavity have received the greatest attention in the recent literature (see, for example, R. A. Hill et al, *Applied Optics*, 13:186 (1974), 16:2004 (1977) and G. Muller et al, *Optik* 56:1 (1980)). The multiple-pass cells reported by Hill et al in 1974 in *App. Opt.* 13:186 typify the optical arrangements used to focus a multiply reflected laser beam into an optical point source. Conventional lens systems (as opposed to a multiple-reflection optical cell) are then used to focus a small portion of the available Raman radiation generated at the intense point source into a spectrometer.

An optical arrangement which combines a multiple-reflection Raman optical cell in a transverse alignment to a multiple-pass laser cell has been suggested by Weber et al in 1967 in *J. Opt. Soc. Am.* 57:19. The multiple-reflection Raman cell proposed was identical to the classical four-mirror design of Welsh et al described hereinbefore. The broad mirror spacing inherent in the classical cell design was poorly compatible in a transverse alignment to the short optical pathlength of the multiple-pass laser cell. No optical design has previously been reported for a multiple-reflection Raman optical cell compatible in a transverse alignment with a multiple-reflection laser cell that is positioned outside a laser cavity. As will be shown in the following description, a unique multiple-reflection Raman cell has been designed by the applicant using a transverse optical alignment to a laser beam contained in a multiple-pass laser cell. The specific design of the multiple-pass laser cell is not a part of this invention.

SUMMARY OF THE INVENTION

It is an object of this invention to provide a unique multiple-reflection optical cell specifically designed for collecting Raman or fluorescence radiation produced by laser excitation of a gas sample inside a multiple-pass laser cell.

Another object of the invention is to provide an optically efficient arrangement of mirrors for collecting radiation from a large optical volume of gas excited by a laser as opposed to a restricted optical point source.

Another object of the invention is to collimate the radiation collected inside a multiple-reflection optical cell and to pass this light through a small portal in the side of the cell in a geometric array compatible with conventional collection optics and detection systems.

Another object of the invention is to provide a simple, rugged, plane-parallel optical arrangement for the mirrors of a multiple-reflection optical cell which requires only one optical alignment mechanism, for the adjustment of the distance between the mirrors.

Another object of the invention is to provide relaxed focusing requirements for the position of the composite laser beam inside a multiple-reflection cell of the type described.

Another object of the invention is to eliminate the collection of scattered light off the multiple-pass laser cell mirrors through the inherent design of the multiple-reflection optical cell.

Other objects of the invention are to: use a simple two-mirror system as opposed to the three, four and eight-mirror systems previously proposed; use only one output aperture to limit losses of radiation from a multiple-reflection cell; and provide a compact optical cell to enhance the sensitivity of a Raman or fluorescence gas analysis.

These objects and certain advantages not available in known gas analysis devices are attained by a preferred embodiment of the invention. The proposed multiple-reflection Raman optical cell consists of two spherical mirrors $M_1$ and $M_2$ positioned in a confronting plane-parallel alignment, transverse to a laser beam being multiply reflected through the optical cell. The mirrors $M_1$ and $M_2$ are of equal diameter, possessing different radii of curvature. The mirror of smaller curvature, $M_2$, possesses a small portal in the center of the mirror. The distance between the mirrors is less than half the radius of curvature of either mirror $M_1$ or $M_2$.

The gas to be analyzed is flowed between the mirrors of the multiple-reflection cell. Laser light is passed back and forth through this gas along the laser axis. A portion of the Raman or fluorescence radiation emanating from the gas excited by the laser is (1) collected by mirrors $M_1$ and $M_2$, (2) partially collimated, and (3) passed through the portal in mirror $M_2$ in a geometric array compatible to conventional collection optics for a spectrometer.

DETAILED DESCRIPTION OF A PREFERRED EMBODIMENT OF THE INVENTION

Figure 1:
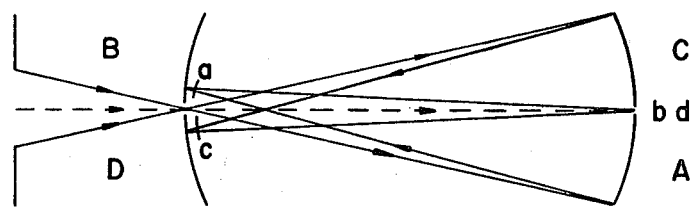
FIG. 1 illustrates a fundamentally important multiple-reflection Raman optical cell design which has been widely cited and applied in both modified and unmodified form with conventional and laser excitation sources.
Figure 2:
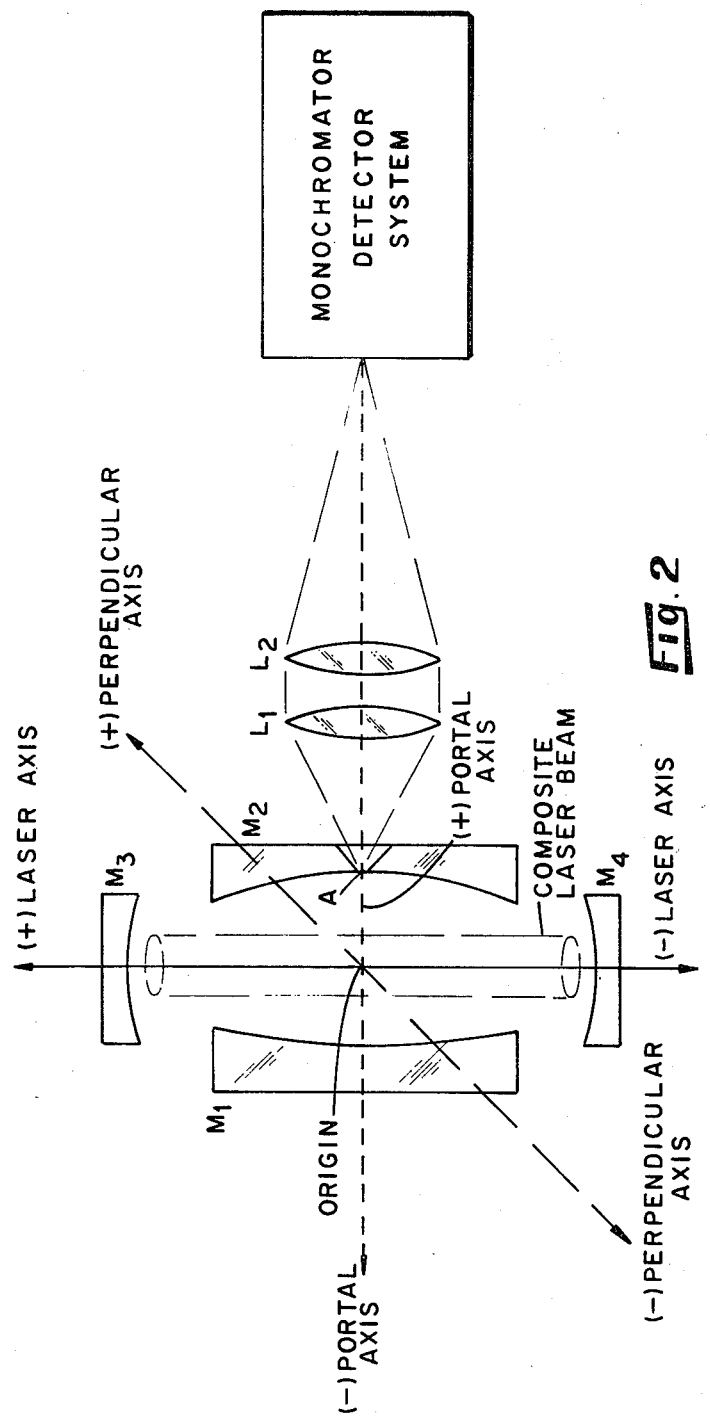
FIG. 2 is a schematic representation of the multiple-reflection optical gas cell in accordance with the invention.

A preferred embodiment of the invention is shown in FIG. 2. It consists of two dielectrically coated spherical mirrors, $M_1$ and $M_2$, each possessing a diameter of 5.1 cm (2 inches). The spherical reflective surface of mirrors $M_1$ and $M_2$ are spaced 2 cm apart in a confronting, plane-parallel alignment, i.e., the spherical reflective surface of mirror $M_1$ faces the spherical reflective surface of $M_2$ and the circular peripheral edges of mirrors $M_1$ and $M_2$ are uniformly separated by a distance of 2 cm. The centers of the mirrors are located on a common axis designated as the portal axis. The radius of curvature of mirror $M_1$ is 30 cm, and the radius of curvature of mirror $M_2$ is 5 cm.

A circular portal, designated A, possessing a diameter of 0.22 cm extends axially through the center of mirror $M_2$. Portal A diverges from a 0.22 cm diameter hole on the spherical reflective surface of mirror $M_2$ at an angle of 50 degrees with respect to the portal axis. The edge thickness of portal A on the spherical reflective surface of mirror $M_2$ is minimized to less than 0.2 mm. A portal in the shape of a square (0.2 × 0.2 cm) possessing similar area may also be used.

Laser light is reflected back and forth along the axis designated the laser axis using conventional means. A pair of mirrors, $M_3$ and $M_4$, positioned outside the multiple-reflection cell and centered on the laser axis is representative of the necessary apparatus. In the preferred embodiment of the multiple-reflection cell the laser light is reflected back and forth through the cell producing a columnar composite light beam designated in FIG. 2. This composite beam is centered along the laser axis equidistant from mirrors $M_1$ and $M_2$, and has a diameter of less than 2 cm (i.e., the distance between $M_1$ and $M_2$ in the preferred embodiment). A complex multiple-pass laser cell which focuses the composite laser beam into one or two points within the multiple-reflection cell may be used but is not required.

Gas to be analyzed is flowed between mirrors $M_1$ and $M_2$. The portion of the gas exposed to the composite laser beam produces Raman and fluorescence radiation which is emitted with random directionality. The design of the invention is such that a significant portion of the Raman or fluorescence radiation produced in a large volume of gas within the cell is reflected back and forth between mirrors $M_1$ and $M_2$ and then directed through aperture A in mirror $M_2$. The vast majority of radiation that exits through aperture A can be collected by a conventional double lens system. Lens $L_1$, the lens closest to the cell, has an F number of 1. Lens $L_2$ has an F number equal to the F number of the monochromation-detector system of FIG. 2.

OPERATION OF THE PREFERRED EMBODIMENT

The operation of the preferred embodiment of the invention was evaluated using a three-dimensional computer simulation program. The optical collection efficiency of the invention was evaluated by testing the efficiency of the cell design for light emanating in randomized direction from points within the cell. A series of 2592 rays originating from each point was tested. Seventy-two equally spaced azimuthal projections were used for each of 36 equally spaced polar angles. Each ray was tracked until it was (1) lost between the mirrors of the cell, (2) exited the portal, or (3) achieved a greater than 99% loss due to the mirror reflectivity. The angle of each ray which exited the portal was tabulated to check its compatability with collection optics of different F number.

Figure 3:
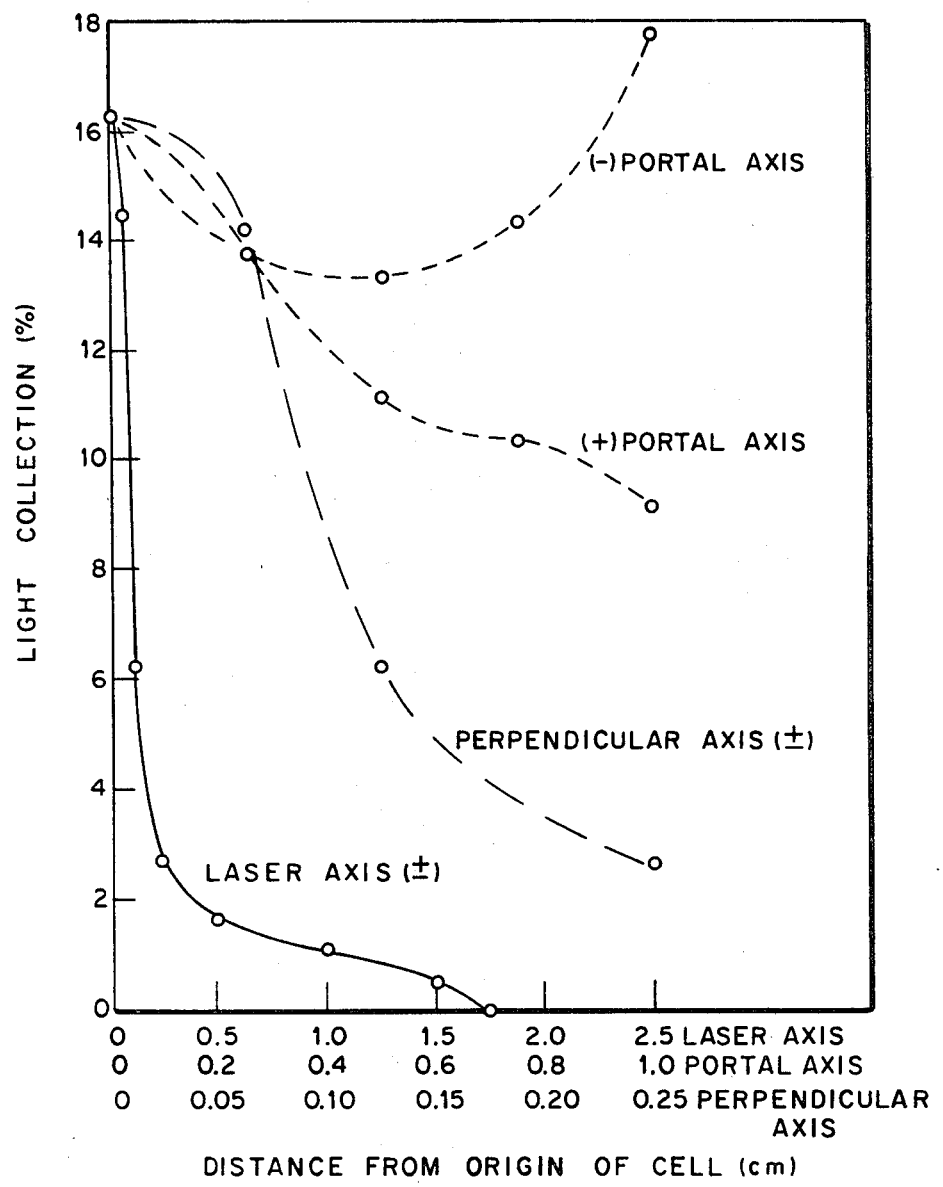
FIG. 3 is a graph illustrating the optical collection efficiency of the cell as a function of position along the laser, portal and perpendicular axes of the cell.

The computed optical collection efficiency of the multiple-reflection cell as a function of distance from the origin of the cell along the laser, portal, and perpendicular axes is shown in FIG. 3. The origin of the cell is the point of intersection of the laser, portal and perpendicular axes in FIG. 2. The perpendicular axis is the axis mutually perpendicular to the laser and portal axes. The computed collection efficiency for points along the three separate axes shown in FIG. 3 are labeled in terms of positive and negative coordinates from the origin of the cell. The scale of distance is different for each axis. Significant collection of light is obtained by the invention from $+1.75$ to $-1.75$ cm on the laser axis. A collection efficiency of approximately 10 to 18% is achieved from $+1$ to $-1$ cm along the available portal axis. The highest collection efficiency on the portal axis is achieved in closest proximity to mirror $M_1$. The collection efficiency along the perpendicular axis demonstrates an identical functionality to that along the laser axis. The collection efficiency for scattered laser radiation from the surface of any multiple-pass cell mirrors, e.g., $M_3$ and $M_4$, is zero provided the mirrors are positioned outside of the multiple-reflection cell.

Figure 4:
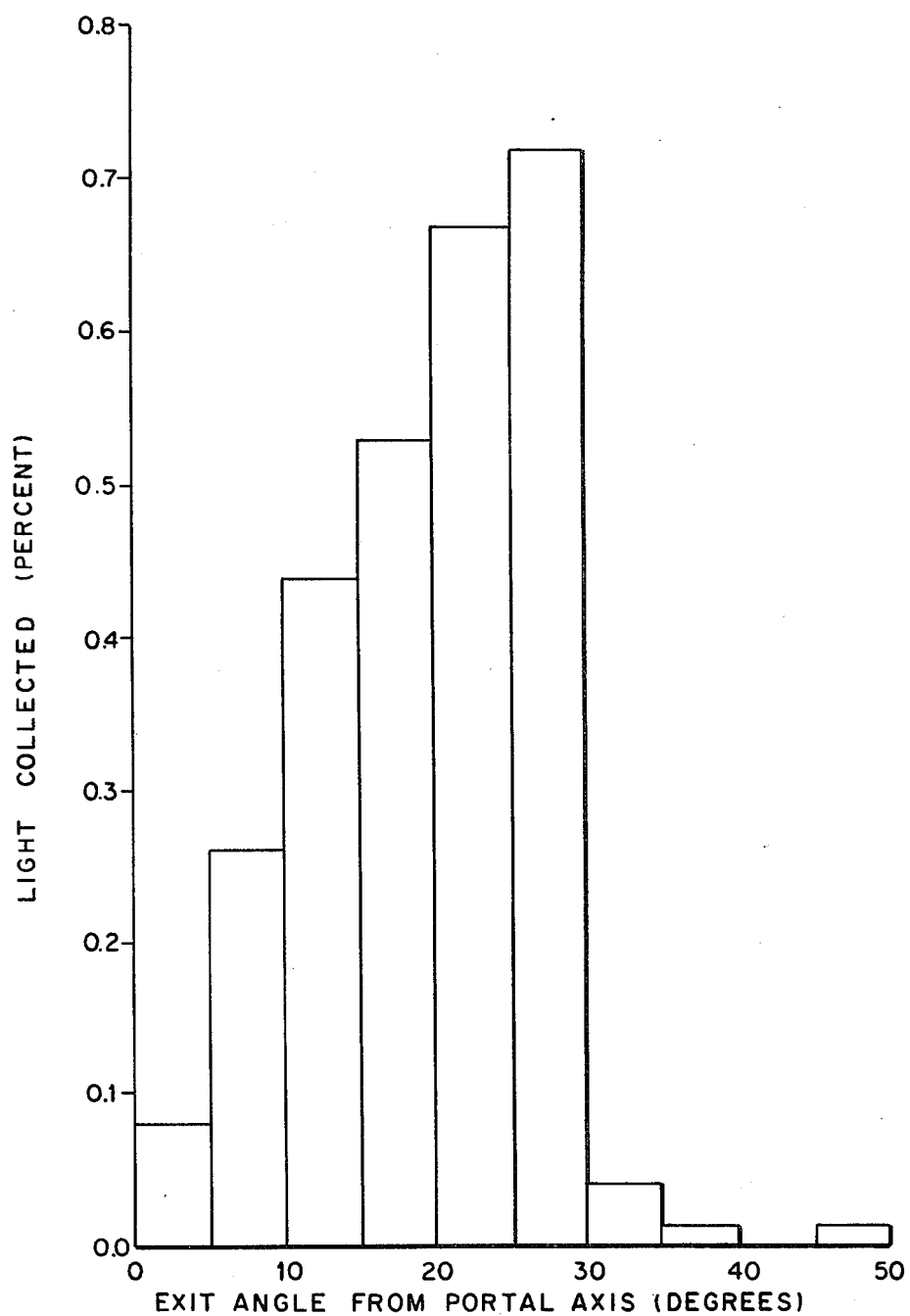
FIG. 4 is a graph illustrating the angular profile of light exiting the portal in mirror $M_2$.

An average collection efficiency was evaluated for light originating from a subset of a 3.5 cm long, 2 cm diameter columnar composite light beam centered along the laser axis. A three-dimensional matrix of 45 points was sampled representing a 3.5 cm$^3$ excitation volume: 5 positions equally spaced along 3.5 cm of the laser axis, 3 positions equally spaced along 2 cm of the portal axis, and 3 positions equally spaced along 0.5 cm of the perpendicular axis. A mirror reflectivity of 99.5% was used. An angular profile analysis (with respect to the portal axis) of the rays exiting portal is shown in FIG. 4. An average collection efficiency of 2% was determined from the sum of the contributions possessing a less than or equal to 25 degree angle (corresponding to F1 collection optics). A mirror reflectivity of 99% resulted in an average collection efficiency of 1.8%. An average optical collection efficiency of about 2% is very high for a 3.5 cm$^3$ optical volume within a multiple-reflection Raman or fluorescence cell.

An envisaged application of the invention is a field-portable Raman spectrometer for the analysis of pollutant gases. The high optical collection efficiency of the multiple-reflection cell design for large optical volumes within the cell makes such an application feasible. The increase in sensitivity will result in a reduction in the laser power requirement. The simple two-mirror, plane-parallel optical alignment and reduced focusing requirements for the multiple-pass laser cell will also enhance the reliability and ruggedness of a field-portable instrument. Envisaged applications of this instrument include the monitoring of toxic sulfur gases in synfuel processing environments.

A second envisaged application of the invention is a chemically selective, universal detector for gas chromatography. All chemical species possess a Raman spectrum. Raman spectroscopy can be used to investigate a specific chemical species, a class of chemical compounds, or all chemical species by adjusting the frequency of Raman radiation which is used. Raman spectroscopy therefore has the potential to be a chemically selective yet universal detection method for gas chromatography. The optical collection efficiency of the invention provides the required enhancement in the sensitivity to make such an application feasible.

A third envisaged application of the invention is a field-portable industrial hygiene monitor for polynuclear aromatic hydrocarbon vapors using synchronous fluorescence spectroscopy. Polynuclear aromatic hydrocarbons represent an occupational hazard in coal processing environments. In the liquid phase they can be analyzed in bulk by fluoescence spectroscopy or in a chemically selective manner by synchronous fluorescence spectroscopy. For gas phase measurements synchronous fluorescence spectroscopy has been impractical for a field-portable instrument because of the limited optical collection efficiency of known fluorescence vapor cells. The multiple-reflection optical cell of this invention provides the necessary enhancement in sensitivity to make this technique feasible for industrial hygiene applications. The use of a conventional light source (xenon lamp) is also envisioned. This would eliminate the requirement of multiple-pass laser cell.

What is claimed is:

1. A multiple-reflection optical cell comprising two spherical mirrors positioned in confronting plane-parallel alignment, said mirrors having different radii of curvature, the center of each of said mirrors being positioned on the optical axis of the cell, the mirror with the smaller radius of curvature having a portal at its center which extends through the mirror along the optical axis of the cell, said optical axis being the axis along which Raman or fluorescence radiation is collected and transmitted to an optical detection apparatus, and said optical axis being perpendicular to the axis along which optical excitation is applied to a gas positioned between the mirrors of the cell.

2. The apparatus of claim 1 wherein said mirrors have the same diameter.

3. The apparatus of claim 1 wherein the spacing between the circular edges of said mirrors is uniform and less than half of the radius of curvature of either mirror.

4. The apparatus of claim 1 wherein said mirrors have a diameter of 2 inches, the circular peripheral edges of said mirrors are uniformly spaced 2 cm apart, one of said mirrors has a radius of curvature of 5 cm, the other of said mirrors has a radius of curvature of 30 cm, and a 0.22 cm diameter portal extends through the center of the mirror with the 5 cm radius of curvature.

5. The apparatus of claim 1 including a non-focused composite light beam for optical excitation of gas flowed between said mirrors, said light beam being (1) contained within the bounds of a columnar beam of less than 2 cm diameter, and (2) centered along an axis which intersects the origin of the cell and is equidistant from the circular peripheral edges of the cell mirrors.

* * * * *